US006972194B1

US006972194B1

(12) United States Patent
Zybin et al.

(10) Patent No.: US 6,972,194 B1
(45) Date of Patent: Dec. 6, 2005

(54) USE OF POLYACRYLAMIDE GEL FOR FORMING A CONNECTIVE-TISSUE CAPSULE IN A MAMMAL FOR CULTIVATING ALLOGENIC AND XENOGENIC CELLS

(76) Inventors: Dmitry Vladimirovich Zybin, ulitsa armavirskaya, 5, kv. 212, Moscow (RU); Alexei Gennadievich Kotelevits, ulitsa Pyatnitskaya, 39, kv.1, Moscow (RU); Vladimir Konstantinovich Sologub, ulitsa Garigaldi, 10, korp. 3, kv.304, Moscow (RU); Ljubov Leonidovna Mironova, Leninsky, raion, pos. "Institut polimelita", 1, kv. 7, Moskovskaya oblast (RU); Sergei Evgenievich Severin, Novye cheremushki, kvartal 24-25, korp. 8B, kv.245, Moscow (RU)

( * ) Notice: Subject to any disclaimer, the term of this patent is extended or adjusted under 35 U.S.C. 154(b) by 0 days.

(21) Appl. No.: 09/890,496

(22) PCT Filed: Nov. 22, 2000

(86) PCT No.: PCT/RU00/00477

§ 371 (c)(1),
(2), (4) Date: Jul. 31, 2001

(87) PCT Pub. No.: WO01/41809

PCT Pub. Date: Jun. 14, 2001

(30) Foreign Application Priority Data

Dec. 8, 1999 (RU) .................................. 99125349
Jun. 23, 2000 (RU) .............................. 2000116208

(51) Int. Cl.[7] .......................... C12N 5/00; C12N 5/08; C12N 5/02
(52) U.S. Cl. ...................... 435/382; 435/366; 435/367; 435/368; 435/369; 435/370; 435/371; 435/373; 435/374; 435/375
(58) Field of Search ............................... 435/366–371, 435/373, 374, 375, 382

(56) References Cited

U.S. PATENT DOCUMENTS 4,353,888 A * 10/1982 Sefton
5,827,707 A * 10/1998 Lamberti .................... 435/178

FOREIGN PATENT DOCUMENTS

| EP | 0742022 | 11/1996 |
| JP | 20004247 | 12/1993 |
| RU | 2026643 | 1/1995 |
| RU | 94033342 | 3/1996 |
| RU | 2090185 | 9/1997 |
| RU | 2135193 | 8/1999 |
| WO | WO 99/10021 | * 3/1999 |

OTHER PUBLICATIONS

Shimizu et al, Artificial Organs, 1996, vol. 20, pp. 1232-1237.*
Gin et al, Journal of Microencapsulation, 1992, vol. 9, pp. 489-494.*
Vacanti et al, The Lancet, 1999, vol. 354, suppl. 1, pp. 32-34.*
Chaikof (Annual Review of Biomedical Engineering, May 1999, vol. 1, pp. 103-127).*
Wang et al (Nature Biotechnology, 1997, vol. 15, pp. 358-362).*
Sefton and Stevenson (Advances in Polymer Science, 1993, vol. 107, pp. 143-197.*
Stedman's Medical Dictionary, 27th Edition, 2000, definition for "vaccine".*
Paul, Fundamental Immunology, (text), 1993, pp. 1157-1170.*
Apostolopoulos et al (Nature Medicine, 1998, vol. 4, pp. 315-320).*
Jager et al (PNAS, 2000, vol. 97, pp. 12198-12203).*
Abstracts of Semino et al (Journal of Biological Regulators and Homeostatic Agents, 1993, vol. 7, pp. 99-105).*
The abstract of Algarra et al International Journal of Clinical and Laboratory Research, 1997, vol. 27, pp. 95-102).*
Bodey et al (Anticancer Research, 2000 Jul.-Aug., vol. 20, pp. 2665-2676).*
Lauritzsen et al (International Journal of Cancer, 1998, vol. 78, pp. 216-222).*
Sarma et al (Journal of Experimental Medicine, 1999, vol. 189, pp. 811-820).*
Ohlen et al (Journal of Immunology, 2001, vol. 166, pp. 2863-2870).*
Antoinia et al (International Immunology, 1995, vol. 7, pp. 715-725).*
Partial English Translation of RU 200 4247 Dated Dec. 15, 1993.
English Translation of the abstract and claim of RU 2090185 dated Sep. 20, 1997.
Shumakov, V.I., et al. "Transplantation of Islet Cells in the Therapy of Diabetes Mellitus" Full Russian Article, p. 109-114, and English Abstract, p. 114 (1998).

(Continued)

*Primary Examiner*—Karen A. Canella
(74) *Attorney, Agent, or Firm*—Ladas & Parry

(57) ABSTRACT

The invention relates to the field of medicine and more particularly it relates to the problem of vaccination against tumor cells and vaccinotherapy of oncological diseases, and also to a method of treating diabetes mellitus. In the invention a new method of cultivating cells is proposed, which contemplates forming a capsule of a polyacrylamide gel in the tissue of an animal, including a human, into which capsule desirable cells are injected. The invention provides for maintaining the viability of cells during a long period of time.

17 Claims, 1 Drawing Sheet

OTHER PUBLICATIONS

English Translation of the abstract and claims of RU 2135193 dated Aug. 27, 1999.

English Translation of the abstract and claim of RU 2026643 dated Jan. 20, 1995.

Souberbielle, B.E., et al. "Comparison of four strategies for tumour vaccination in the B16-F10 melanoma model" Gene Therapy, vol. 5, p. 1447-1454, (1998).

Lanza, R.P., et al. "Transplantation of islets using microencapsulation: studies in diabetic rodents and dogs," J. Mol. Med., vol. 77, No. 1, p. 206-210, (1999) Abstract only.

Gajewski, T.F., et al. "Rational development of tumour antigen-specific immunization in melanoma" Therapeutic Immunology, vol. 2, p. 211-225, (1995).

Skaletskii, N.N., et al. "The effect of cultivating islet cells of the pancreas on their survival in the organism of a xerogenous recipient" p. 8-9. (1995).

Volkov, I.E. et al. "Preliminary Results of Xenogeneic Grafting of Cultures of Pancreatic Islet . . . " Institute of Transplantology and Artifical Organs, Ministry of Health, Moscow (1998) pp 105-108.

* cited by examiner

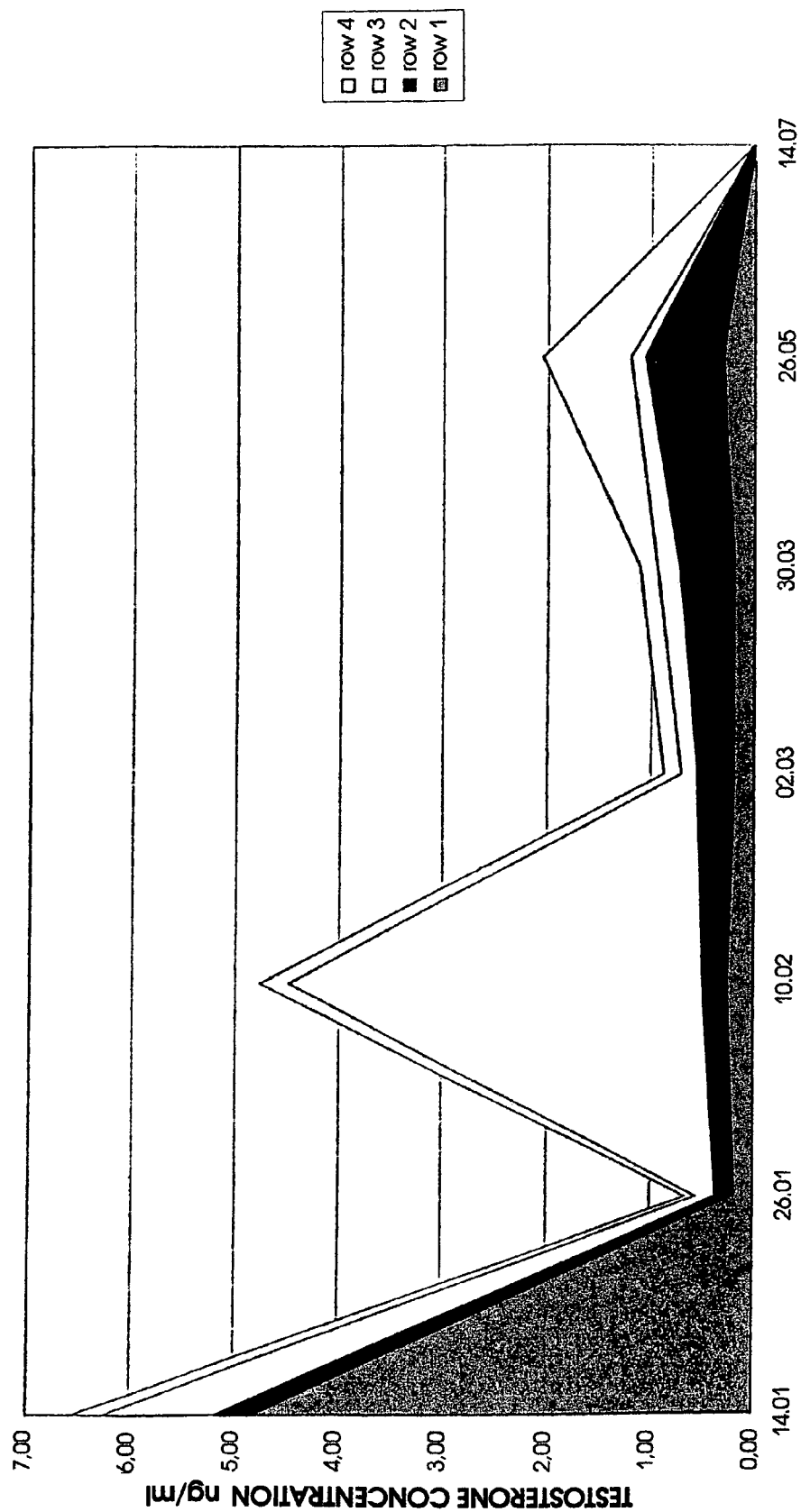

USE OF POLYACRYLAMIDE GEL FOR FORMING A CONNECTIVE-TISSUE CAPSULE IN A MAMMAL FOR CULTIVATING ALLOGENIC AND XENOGENIC CELLS

The present invention relates to medicine, particularly to immunology and immunooncology, and also to the treatment of diabetes mellitus, predominantly of insulin-dependent diabetes mellitus. More particularly, the invention relates to the problem of vaccination against tumor cells and of vaccinotherapy of oncological diseases and to a new method of treating diabetes mellitus. Furthermore, the invention proposes a special capsule for use in methods of treating, owing to which the treatment proves to be substantially more effective.

It is known that the problem of transplanting organs, tissues, cell cultures of mammals involves difficulties associated with the possibility of xenogenous tissue-and-cell agents to "take root" in the recipients' organism. The existing methods of transplanting allo-, hetero- and xenotransplants require either powerful immunosuppressive therapy of the recipient or original procedures. These latter comprise methods of transplanting cells of various organs of human and animal fetuses, i.e., the effect of undeveloped species specificity is employed. In such a manner, e.g., islet cell cultures of the pancreas of 24–26 weeks' human fetuses are transplanted into the parenchyma of the liver or into the portal vein in experiments with rats.

The place of introducing cells may be splenic pulp or muscles of the anterior abdominal wall. Cases of treating humans suffering from diabetes mellitus by a similar method are known (Skaletskii N. N., "The Effect of Cultivating Islet Cells of the Pancreas on Their Survival in the Organism of a Xenogenous Recipient", in: All-Russian Conference on Transplantation of Organs, 1995, pp. 219–220 (in Russian)).

The transplantation of Leydig's cells into testicular tissue to males for treating infertility is of interest, because the rejection reaction does not occur due to the presence of a hematotesticular barrier (Zybin D. V, "Method of Treating Patients with Dysfunction of Male Sexual Sphere by Transplantation Techniques", RF Patent 2026643 of 20.01.95).

As a result of both above-described methods, good results were obtained in preserving the viability and activity of transplanted cells. However, the first method makes it possible to use only embryonal cells, this, for obvious reasons, involving a number of difficulties; the second method of cell therapy proves to be applicable only to male individuals.

There is known a method of vaccination and vaccinotherapy of tumors with the help of live cells. The employed cells are hybridomas or transformed cells, allogenic or autogenic. A disadvantage of such cells is their short-time existence in the organism and, correspondingly, a low immunizing effect (B. E. Souberbielle, M. Westby, S. Ganz, and J. Kayaga, Comparison of four strategies for tumor vaccination in the B-16

F 10 melanoma model. Gene Therapy 1998, 1447–1454).

Known in the art is a method of transplantation of pancreatic islets (PIs) using microencapsulation.

The method consists in introducing (allo- or xenogenic) PIs encapsulated in spheres of an alginate gel. The spheres are implanted intraperitoneally. The implantation of spheres completely replaces insulin therapy during 175 days, but in this case immunosuppressive therapy is concurrently used. Bovine PIs are administered to rats with induced diabetes without immunosuppression. Normoglycemia is maintained from several weeks to one month.

A certain inconvenience of the method is the necessity of using immunosuppressive therapy. Definite difficulties are involved in preparing capsules in vitro (Lanza R. P., Esker D. M., and Marsh J. P., Transplantation of islets using microencapsulation studies in diabetic rodents and dogs. J. Mol. Med., 1999 Jan. 77(1): 206–10).

Also known is a method of vaccination and vaccinotherapy of tumors with the help of live cells. It consists in producing hybridomas of tumor cells and allogenic dendritic cells (or macrophages). The obtained hybridomas are used as vaccine preparations.

However, this method also features a low immunizing effect, caused by the short-time existence of the introduced cells in the recipient's organism (Gajewsky T. F. and Fallarino F., Rational development of tumor antigen-specific immunization in melanoma. Therapeutic Immunology, 1997, 2, 211–225).

Therefore, the problem of increasing the life-span of transplanted cells and, as a consequence, of enhancing the immunizing effect, as well as obviating immunosuppressive therapy is now as before topical in this field of the art.

Specialists are aware that the problem of treating diabetes mellitus is also closely connected with the positive solution of the question of transplanting cells, whose successful solution will in many respects make for the desired effectiveness of the method of treating.

For instance, a method of treating diabetes mellitus is known, according to which implantation of cells of benignant human insulinoma is carried out, the material containing pancreatic β-cells is implanted into the musculus rectus abdominis (RF Patent 2004247).

However, problems which arise in connection with combating the predominance of the growth of fibroblasts when using a culture of β-cells for transplantation, and the necessity of precise control of the insulin production by a particular fraction of the insulinoma cell culture, called for due to the fact that tumor cells whose functional activity may vary substantially are used as the implant, offer a hindrance to the wide use of the method.

Also known is a method of treating diabetes mellitus by transplanting material containing pancreatic β-cells (RF Patent 2135193). The method of treating diabetes mellitus, predominantly insulin-dependent one, is carried out using material containing pancreatic β-cells of mammals, produced with the use of the β-cells migration phenomenon.

The material containing pancreatic β-cells is transplanted into different organs and tissues; intramuscularly, into the musculus rectus abdominis, into the liver (into the parenchyma or via the portal vein), into the splenic pulp, into the spleen artery, into the abdominal cavity, into the greater omentum, into a specially created muscular pocket.

The short period of time during which β-cells produce an insulin donor in the recipient's organism because of the effect of rejection of heterogeneous cells necessitates considerable immunosuppressive therapy.

FIG. 1 illustrates the dynamics of testosterone in the blood serum of Vistar-line rats to which Leydig's cells of young pigs (rows 1 and 2) and of green monkeys (rows 3 and 4) are implanted. Rows 1 and 3 show control results (cells are introduced subcutaneously, rows 2 and 4 show experimental results (introducing cells into a formed polyacrylamide capsule).

The present invention is directed to overcoming the above-indicated problems. The authors of the present invention unexpectedly discovered that long-time maintaining the viability of transplanted cells, including heterogeneous ones, in the recipient's organism can be provided by using a polyacrylamide gel capsule being formed in vivo in the organism of a mammal (including a human) in need of therapy with such cells.

So, one of the aspects of the present invention is the use of a polyacrylamide gel for preparing in the organism of a mammal a polyacrylamide capsule formed therein in vivo, which capsule can later be used for cultivating cells transplanted thereinto.

Unexpectedly to the authors of the present invention, cells injected into the above-said capsule proved to be capable of preserving viability for a long period of time (to 100 days and more) and of producing compounds necessary for the treatment.

Another aspect of the invention is, therefore, a method of cultivating cells necessary for the treatment in the organism of a patient in need of such treatment. The cultivation of cells is preceded by the injection of a polyacrylamide gel into the organism of a mammal; by the formation of a gel capsule during a definite period of time in the organism of a mammal; and by the injection into said capsule of a required amount of cells to be transplanted.

Long-time survival of the cells in the cultivation thereof inside the patient's body proves to be useful for the treatment of a number of diseases, which requires transplantation of autologous or heterologous (allogenic and xenogenic) cells producing biologically active compounds whose deficiency in the organism aggravates or initiates the disease.

The third aspect of the present invention is a method of treating diseases for which immunization with an antigen is indicated, this antigen under usual conditions requiring intensive immunosuppressive therapy.

The next aspect of the invention is a method of treating diabetes mellitus, predominantly insulin-dependent one, consisting in that an effective amount of pancreatic β-cells is introduced into a polyacrylamide gel capsule preformed in the organism of a patient.

One more aspect of the present invention is a method of cultivation and modification of heterogeneous cells (tumor cells, Leydig's cells, etc.) in the organism of a mammal with a view to their subsequent use for producing a vaccine preparation. The definition "modification of heterogeneous cells" should be understood as lowering the proliferative activity and immunizing action on the organism.

The invention will further be disclosed in detail by examples of its preferred embodiment, these examples being given by way of illustration only and should not be used for limiting the scope of claims. A person skilled in the art may find a considerable number of possibilities for complementing or modifying the invention which will preserve the above-indicated advantages and will be encompassed by the set of claims.

In a general form the invention is carried out as follows.

A connective-tissue capsule according to the present invention may be formed, for instance, by way of subcutaneous injection of a polyacrylamide gel (PAAG) (in a volume of 1.0–5 ml) to animals, e.g., to Vistar-line rats (in a volume of 1.0–3 ml) or (in a volume of 0.5–1 ml) to mice of C57BLACK and BALB/C lines or to a mammal such as a human (in a volume of 1.0–3.0 ml). Individuals of different sexes may participate in the experiment. Leydig's cells of pubescent young pigs, rats, and green monkeys or tumor cells can be introduced into the gel capsule. Animals to which cells are injected subcutaneously serve as control.

A suspension of viable Leydig's cells from the testicles of pubescent young pigs, rats, and green monkeys is prepared by using solutions containing a nutrient substrate for cells, in particular, compositions of standard Eagle's medium, medium 199, Hanks' solution, etc.

The essence of the proposed method of treating patients suffering from diabetes mellitus is the long-time existence of and production of insulin by pancreatic β-cells of the donor in the recipient's organism, this being achieved by preliminary subcutaneous injection of a polyacrylamide gel to the patient and subsequent transplantation of β-cells into the formed capsule.

The material for the transplantation of β-cells is obtained from the pancreas of mammals (newborn pigs, rabbits, pubescent green monkeys). Cultivation is carried out using standard media and solutions. For preserving P-cells in the active state, a method of sparing enzymatic treatment of the pancreas is employed, which consists in alternating contacts of the tissue with the enzyme and the nutrient medium. As a result of the treatment steps, fragments of the pancreas tissue and β-cells are introduced into cultivation vessels without centrifugation. Disaggregation of the tissue is carried out with a 0.1–0.25% solution of trypsin and chenopsin in different sequences, depending on the donor material. The enzymatic treatment of the tissue is completed during its contacts with the medium, using a "Biotech-m" flask, which provides for controlled stirring of the suspension on a magnetic table.

The resulting cell material is injected to the patient into the connective-tissue capsule which is formed by the polyacrylamide gel preliminarily administered subcutaneously. The amount of the cells depends on the gravity of the recipient's disease.

THE EXAMPLES WHICH FOLLOW ILLUSTRATE CARRYING THE INVENTION INTO EFFECT

Example 1

A culture of Leydig's cells of newborn pigs in the volume of 0.5 ml with the concentration of cells of 5 million per ml is injected into a polyacrylamide gel capsule to females of Vistar-line rats.

To the control group of animals of the same line, sex and anthropological data a culture of Leydig's cells of newborn pigs is administered subcutaneously. Before injecting the cell culture, the content of testosterone in the blood serum of the animals is measured. Subsequent measurements of testosterone in the blood serum are carried out with different intervals during 7 months in the control and experimental animals simultaneously.

The number of animals in control and in the experiment was 2 individuals in each. FIG. 1 (rows 1 and 2, respectively).

Example 2

A culture of Leydig's cells of pubescent green monkeys in the volume of 0.5 ml with the concentration of cells of 5 million per ml is injected into a polyacrylamide gel capsule to females of Vistar-line rats.

To the control group of animals of the same line, sex and anthropological data a culture of Leydig's cells of pubescent green monkeys is administered subcutaneously. Before injecting the cell culture, the content of testosterone in the blood serum of the animals is measured. Subsequent measurements of testosterone in the blood serum are carried out with different intervals during 7 months in the control and experimental animals simultaneously.

The number of animals in control and in the experiment was 2 individuals in each. FIG. 1 (rows 1 and 2, respectively).

After 7 months of observations the animals are sacrificed and a histological investigation is carried out. It indicates the presence of a large amount of viable Leydig's cells, so that a conclusion can be drawn about the possibility of vital activity of xeno- and heterogeneous cells in the recipient's organism with the use of a gel.

Example 3

PAAG in the volume of 0.5 ml is administered subcutaneously to an experimental group of mice of the BALB/C line (6 individuals). Tumor cells of murine melanoma B-16 are injected into the gel in the volume of 1 ml with the concentration of cells of 1 million cells per ml. Cells of murine melanoma B-16 in the volume of 1 ml with the concentration of cells of 1 million per ml are administered subcutaneously to a control group of mice of the BALB/C line (6 individuals).

It is known that in mice of the BALB/C line the tumor of murine melanoma B-16 does not grow. In the control group of the animals the tumor growth was found in none of the 6 individuals. In the experimental group of the animals, by way of palpatory examination, a growth of tumor in the PAAG was noted in all the 6 individuals. By the 60th day the experimental animals with the murine melanoma B-16 in the gel are sacrificed. The gel with tumor cells is extracted under aseptic conditions and transferred to a monolayer culture on the nutrient medium RPMI-1640 with 10% fetal serum. Fragments of the capsule with the tumor cells are fixed in a neutral solution of formalin, and a histological investigation is carried out, which allows one to judge about a higher differentiation of melanoma cells and the loss of the proliferative activity by them (Table 1

TABLE 1

COMPARISON OF THE GROWTH OF MELANOMAS B-16 (MURINE) AND SKMEL 28 (HUMAN) IN MICE OF BALB/C AND C57BLACK LINES

| LINE OF MICE | TUMOR STRAIN | GROWTH OF MELANOMA | SPAN OF LIFE | META-STASES |
|---|---|---|---|---|
| BALB/C + GEL | B-16 | + | 60 DAYS (observation period)* | – |
| BALB/C | B-16 | – | > OBSERVATION PERIOD | – |
| C57BLACK + GEL | SKMEL28 | + | > OBSERVATION PERIOD | – |
| C57BLACK | SKMEL28 | – | > OBSERVATION PERIOD ** | – |

*Animals with tumors grown in the gel are sacrificed. The tumor cells isolated from them are used in the next experiment (Table 2).
**Mice are used further in the experiment for estimating immunity against melanoma B-16 (Table 3).

Example 4

A culture of cells prepared as in Example 1 is administered subcutaneously in the amount of 1 ml with the concentration of cells of 1 million to mice of the C57BLACK line (6 individuals).

It is known that in mice of the C57BLACK line the tumor of murine melanoma B-16 grows in 100% of cases, death of the animals occurs on the 20–25th day in 100% of cases.

To the control group of C57BACK mice a culture of cells of murine melanoma B-16 is administered in the amount of 1 ml with the concentration of cells of 1 million.

In experimental mice the appearance of symptoms of tumor growth is noted in 60–65 days; in control mice, in 20–23 days (Table 2).

TABLE 2

TUMORIGENIC ACTIVITY OF MELANOMA B-16, CULTIVATED IN A GEL CAPSULE, IN MICE OF BALB/C LINE, GRAFTED TO MICE OF C57BLACK LINE

| No. | TUMOR STRAIN | TIME OF TUMOR APPEARANCE | LIFE-SPAN OF MICE | PRESENCE OF META-STASES |
|---|---|---|---|---|
| 1 | Melanoma from gel of mice of BALB/C line (B-16-X) | 30 DAYS | 60 DAYS | + |
| 2 | B-16 (control) | 7 DAYS | 22 DAYS | + |

Example 5

PAAG in the volume of 0.5 ml is injected subcutaneously to mice of the C57BLACK line (6 individuals). A cell culture of human melanoma SKMEL is injected into the gel in the amount of 1 ml with the concentration of cells of 1 million.

The control group of mice of the same line (6 individuals) is administered subcutaneously a cell culture of human melanoma SKMEL28 in the volume of 1 ml with the concentration of cells of 1 million.

It is known that the cell culture of human melanoma does not grow in mice in 100% of cases. In the experimental group of animals the tumor growth in the gel is determined by palpation on the 15–20th day after the injection. In the control animals no tumor growth is found (Table 1 [3–4]).

Example 6

The group of experimental animals (6 individuals), described in Example 3, is administered subcutaneously a cell culture of murine melanoma B-16 in the volume of 1 ml with the concentration of cells of 1 million. The control group of mice of the C57BLACK line (6 individuals) is administered subcutaneously a cell culture of murine melanoma B-16 in the volume of 1 ml with the concentration of cells of 1 million.

In the control animals subcutaneous melanomas approximately 3–5 cm in diameter develop on the 7–15th day. In the experimental animals no symptoms of tumor are detected during the same period of time (Table 3).

TABLE 3

IMMUNOGENIC ACTIVITY OF HUMAN MELANOMA SKMEL28 FOR MICE

| No. | TUMOR STRAIN | TUMOR APPEARANCE TIME | DEATH OF ANIMALS |
|---|---|---|---|
| 5 | B-16 | — | >60 DAYS |
| 6 | B-16 | 7–15 DAYS | 18–20 DAYS |

So, the results presented hereinabove give grounds to believe that the method of cultivating heterogeneous cells in PAAG in vivo, whereby the proliferative activity of tumor cells lowers and the cultivated cells produce an immunizing effect on the organism, can be used for vaccination and vaccinotherapy.

Example 7

Female patient F., aged 37. Insulin-dependent diabetes mellitus was diagnosed 11 years ago, one year after the parturition. The pregnancy was aggravated by toxicosis during the second half of the pregnancy period, by nephropathology, a considerable, to 26 kg, gain in weight. The character of the disease has been unstable all these years, and considerable efforts were required in choosing adequate insulin therapy. The use of exogenous insulin was varied from 58 units per day to 30 units per day. During the last two years pathological changes in the kidneys were diagnosed, defined as diabetic nephropathy. In urinalyses a 10–12-fold increase of the upper boundary of proteinuria is noted. The arterial pressure increases to 170/110 mm Hg.

A culture of pancreatic cells of newborn rabbits was administered to the patient subcutaneously, by injecting the culture into a preliminarily formed capsule. Already 7 days later the patient noted an improvement in the general condition, a reduction of the sensation of thirst and dryness of the mucous membrane of the oral cavity, lowering of the arterial pressure down to 140/90 mm Hg. In 15 days the condition of the patient was such that the need in exogenous insulin could be lowered from 30 units to 18 units (blood and urine control). In 30 days the need in exogenous insulin lowered to 12 units per day, and towards the close of the 2nd month, to 4 units per day.

The patient's condition has been followed-up during 12 months. No clinical manifestations of nephropathy are detected, the arterial pressure is within the age norm. The patient was transferred to oral taking of anti-diabetic preparations with obligatory observance of diabetic diet and control of glucose in blood, in urine, as well as of glycosylated hemoglobin.

Example 8

Male patient K., aged 52. Insulin-dependent diabetes mellitus was diagnosed since the age of 18 against the background of a strong stress situation. At first the character of the disease was unstably severe. The doses of exogenous insulin reached 70 units per day. In recent years the course of the disease has stabilized, but worsening of the state occurred after stress situations and errors in the diet.

During the last three years worsening of the state of the vessels of the lower extremities, lowering of the libido, worsening of the erection and deterioration of the coitus quality were observed. Diabetic angiopathy of the lower extremities and penis was diagnosed. During the last year the need in exogenous insulin was from 20 units per day to 40 units per day.

The patient was administered with a culture of pancreatic cells of 14-days' pigs, injected into a preliminarily formed capsule. Two weeks later the patient noted a improvement in the general condition. In one month the need in exogenous insulin lowered to 12 units per day. In 2 months this need lowered to 6 units per day. Four months after the transplantation the patient was transferred to oral taking of anti-diabetic preparations. The sexual life of the patient normalized, the condition of the vessels of the lower extremities improved appreciably.

The subjective and objective symptoms of examined patients, the data of additional methods of blood and urine investigation allow one to speak of a high effectiveness of this method of treating diabetes mellitus, this leading to substantial reduction of the doses of exogenous insulin taken by the patients, and in some cases even to refusal of insulin therapy. The method does not require immunosuppressive therapy, lowers the risk of secondary complications of diabetes mellitus: rethino-, neuro-, nephropathies. The method makes it possible to improve appreciably the quality of life of patients. As a rule, the therapeutic effect lasts for 10–20 months, depending on the severity of the disease.

The amount of cells to be transplanted also depends on the severity of the course of diabetes mellitus, particularly on the quantity of exogenous insulin taken by the patient.

The proposed invention makes it possible, using "a polyacrylamide gel", by introducing it into the organism of a mammal, to form in vivo a capsule, which later on, being injected with viable cells for transplantation, functions as a chamber for cultivating producer cells during a long period of time, required for treating with a compound produced by the cell, when said compound, releasing from this artificially formed chamber, produces the desired effect on the organism of a patient. The use of a polyacrylamide gel for the indicated purposes allows maintaining the viability of cultivated cells for a long time and thereby provides a prolonged curative effect. Said use makes it possible to rule out immunosuppressive therapy and may find very extensive application in practical medicine.

What is claimed is:

1. A method of forming in a mammal a connective tissue capsule for maintaining transplanted allogenic or xenogenic cells comprising introducing a polyacrylamide gel into a tissue of the mammal so as to cause the connective tissue capsule to form around the polyacrylamide gel, wherein the mammal suffers from a pathology and the method comprises introducing into and maintaining in said connective tissue capsule transplanted allogenic or xenogenic cells that aid in treating the pathology.

2. A method according to claim 1, wherein the mammal is a human.

3. A method according to claim 1, wherein the pathology is diabetes mellitus.

4. A method according to claim 1, wherein pancreatic B-cells are introduced into and maintained in said connective tissue capsule.

5. A method according to claim 4, wherein the pancreatic β-cells are cells from rabbits or pigs.

6. A method according to claim 1, wherein the connective tissue capsule is formed by subcutaneous injection of the polyacrylamide gel into the mammal.

7. A method of introducing allogenic or xenogenic cells into a mammal, comprising introducing a polyacrylamide gel into a mammal, thereby inducing formation of a connective tissue capsule around said gel, and thereafter, injecting allogenic or xenogenic cells of a mammal into said connective tissue capsule.

8. A method according to claim 7, wherein the gel is introduced by subcutaneous injection.

9. A method according to claim 7, wherein said allogenic or xenogenic cells are tumor cells.

10. A method according to claim 7, wherein said allogenic or xenogenic cells are Leydig's cells.

11. A method of treating a pathology in a mammal, comprising introducing a polyacrylamide gel into a mammal, thereby inducing formation of a connective tissue capsule around said gel; and thereafter transplanting allogenic or xenogenic cells of a mammal into said connective tissue capsule, said cells being maintained in said capsule and producing a biologically active substance which is released from said capsule for treatment of the pathology.

12. A method according to claim 11, wherein said pathology is diabetes melitus, said transplanted cells are pancreatic β-cells, and said biologically active substance is insulin.

13. A method according to claim 12, wherein said β-cells are from rabbits or pigs.

14. A method of forming in a mammal a connective tissue capsule for maintaining transplanted allogenic or xenogenic cells comprising introducing a polyacrylamide gel into a tissue of the mammal so as to cause the connective tissue capsule to form around the polyacrylamide gel further comprising transplanting allogenic or xenogenic cells into the connective tissue capsule so as to maintain the cells in the capsule for a period of time.

15. A method according to claim 14, wherein said period of time exceeds a period that said transplanted cells would persist in the mammal without prior formation of said connective tissue capsule.

16. A method according to claim 7, wherein said transplanted cells are injected into said capsule such that they persist in the mammal for a period that exceeds a period that said transplanted cells would persist without prior formation of the connective tissue capsule.

17. A method according to claim 11, wherein said transplanted cells persist in the mammal for a period of time that exceeds a period that said transplanted cells would persist without prior formation of the connective tissue capsule.

* * * * *